United States Patent [19]

Engelhardt

[11] 3,992,445

[45] Nov. 16, 1976

[54] 5-FORMAMIDOMETHYL-5H-DIBEN-ZO[A,D]CYCLOHEPTENE DERIVATIVES

[75] Inventor: Edward L. Engelhardt, Gwynedd Valley, Pa.

[73] Assignee: Merck & Co., Inc., Rahway, N.J.

[22] Filed: Aug. 21, 1973

[21] Appl. No.: 390,277

Related U.S. Application Data

[60] Division of Ser. No. 283,680, Aug. 25, 1972, abandoned, which is a continuation of Ser. No. 74,140, Sept. 21, 1970, abandoned, which is a continuation of Ser. No. 656,657, July 28, 1967, abandoned, which is a continuation of Ser. No. 422,488, Dec. 31, 1964, abandoned.

[52] U.S. Cl. ............... 260/556 AR; 260/570.8 TC; 260/562 R; 424/321; 424/324
[51] Int. Cl.² .................................... C07C 103/127
[58] Field of Search ........................... 260/562, 556

[56] References Cited
UNITED STATES PATENTS 3,281,469  10/1966  Peters et al. .................. 260/570.8
3,401,192  9/1968  Kollonitsch et al. ............... 260/562

OTHER PUBLICATIONS

Kawazu, Chem. Abst., vol. 53, Col. 317–318 (1959).

Winthrop et al., J. Org. Chem., vol. 27, pp. 230–240 (1962).

*Primary Examiner*—Natalie Trousof
*Attorney, Agent, or Firm*—Harry E. Westlake, Jr.; Thomas E. Arther; William H. Nicholson

[57] ABSTRACT

This invention relates to derivatives of dibenzocycloheptenes. In particular, the invention relates to dibenzocycloheptenes which are substituted at the 5-position with an aminomethyl group and to methods of preparing the same. The invention also relates to intermediates which are useful in the preparation of the above compounds and to methods for preparing the same.

5 Claims, No Drawings

5-FORMAMIDOMETHYL-5H-DIBENZO[A,D]CY-CLOHEPTENE DERIVATIVES

This is a division of application Ser. No. 283,680, filed Aug. 25, 1972 now abandoned, which is a continuation of U.S. Ser. No. 74,140, filed Sept. 21, 1970 and now abandoned, which is in turn a continuation of Ser. No. 656,657, filed July 28, 1967 and now abandoned, which Ser. No. 656,657 is a continuation of Ser. No. 422,488, filed Dec. 31, 1964 and now abandoned.

This invention relates to derivatives of dibenzocycloheptenes. In particular, the invention relates to dibenzocycloheptenes which are substituted at the 5-position with an aminomethyl group and to methods of preparing the same. The invention also relates to intermediates which are useful in the preparation of the above compounds and to methods for preparing the same.

The end compounds included within the scope of the present invention may be represented structurally as follows:

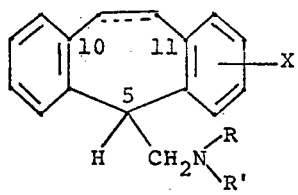

wherein X may be hydrogen, halogen, alkyl (preferably having up to 5 carbon atoms), trifluoromethyl, alkoxy (preferably having up to 5 carbon atoms), alkylsulfonyl (preferably having up to 5 carbon atoms), alkyl mercapto (preferably having up to 5 carbon atoms), and dialkyl sulfamoyl (preferably having up to 4 carbon atoms), R is hydrogen or methyl, R' is hydrogen or methyl. The dotted line in the above formula indicates that the compounds may be saturated or unsaturated at the designated positions. Also included within the scope of this invention are the non-toxic pharmaceutically acceptable salts of the above compounds, the preferred salts being the non-toxic acid addition salts such as the hydrochloride, maleate and the like.

Illustrative of the end compounds included within the scope of the invention are 5-(methylaminomethyl)-5H-dibenzo[a,d]cycloheptene, 10,11-dihydro-5-(methylaminomethyl)-5H-dibenzo[a,d]cycloheptene, 10,11-dihydro-5-(aminomethyl)-5H-dibenzo[a,d]cycloheptene, 10,11-dihydro-5-(dimethylaminomethyl)-5H-dibenzo[a,d]cycloheptene, 5-(methylaminomethyl)-3-methylsulfonyl-5H-dibenzo[a,d]cycloheptene, 5-(methylaminomethyl)-3-trifluoromethyl-5H-dibenzo[a,d]cycloheptene, 5-(methylaminomethyl)-3-methylmercapto-5H-dibenzo[a,d]cycloheptene, 5-(dimethylaminomethyl)-3-methylsulfonyl-5H-dibenzo[a,d]cycloheptene, 5-(dimethylaminomethyl)-3-trifluoromethyl-5H-dibenzo[a,d]cycloheptene, 5-(dimethylaminomethyl)-3-methylmercapto-5H-dibenzo[a,d]cycloheptene, 10,1-dihydro-5-(dimethylaminomethyl)-3-methyl-5H-dibenzo[a,d]cycloheptene, 3-chloro-10,11-dihydro-5-(dimethylaminomethyl)-5H-dibenzo[a,d]cycloheptene and 5-(dimethylaminomethyl)-3-methoxy-5H-dibenzo[a,d]cycloheptene.

The compounds represented above, in either their free base or salt form possess useful pharmacological properties. In particular, they have been found to possess anti-convulsant activity. As anti-convulsants, they may be administered orally in the forms of tablets, powders, sustained release pellets and the like or they may be administered orally or parenterally in the form of aqueous solutions or suspensions. Such formulations may be prepared in conventional manner employing conventional pharmaceutical carriers and excipients. When administered orally or parenterally, satisfactory results are obtained at a daily dosage level of from about 50 mg. to about 500 mg., preferably given in divided doses over the day or in sustained release form. The compounds are preferably administered in the form of their non-toxic acid addition salts.

The compounds represented by the above structural formula may be prepared as illustrated below:

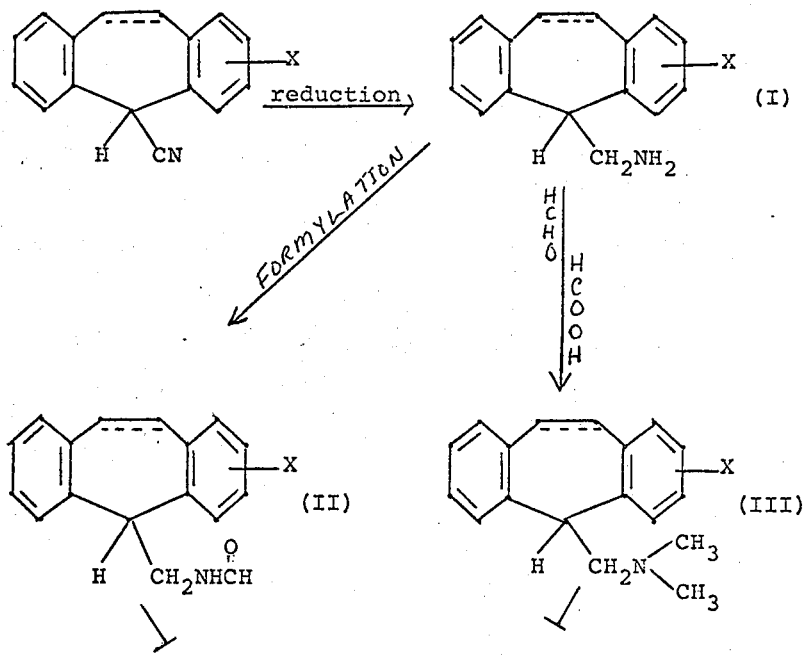

-continued

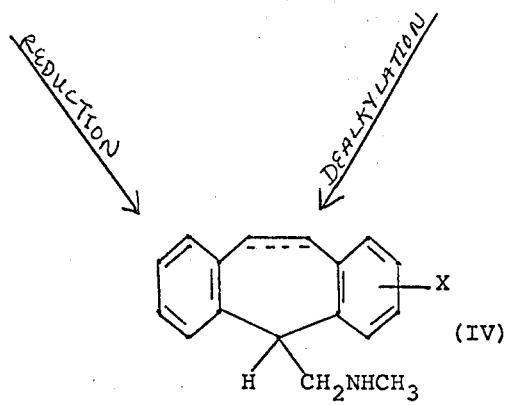

(IV)

wherein the definition of X and the significance of the dotted line are as previously indicated. As is evident from the above reaction sequence, the unsubstituted aminomethyl derivative (I) is obtained by reduction of the corresponding 5-cyano substituted dibenzocycloheptene. The reduction is readily effected by contacting the 5-cyano compound with lithium aluminum hydride in the presence of a suitable inert organic solvent such as tetrahydrofuran, ether or other solvent conventionally employed with lithium aluminum hydride. Preferably this reduction is carried out in the presence of aluminum chloride and an ether compatible with aluminum chloride as a solvent. The temperature at which the reduction is carried out is not critical but it is preferred to employ elevated temperatures up to about 50° C. The resulting aminomethyl derivative is readily recovered employing conventional techniques. The 5-formamidomethyl derivative (II) is prepared by formylation of the aminomethyl compound (I) employing conventional conditions and agents, such as formic acid or esters thereof, for this purpose. The resulting formamidomethyl derivative can be recovered in conventional manner. The dimethylaminomethyl derivative (III) is readily prepared by the treatment of the primary amine compound (I) with formaldehyde and formic acid in accordance with the known Eschweiler-Clarke modification of the Leuckart Reaction. Recovery of the dimethylaminomethyl derivative is accomplished in conventional manner. The methylaminomethyl compounds (IV) may be prepared by either reduction of the formamidomethyl derivative (II) or by monodealkylation of the dimethylaminomethyl derivative (III). Reduction of the formamidomethyl derivative is effected under the first described conditions set forth above for carrying out the reduction of the 5-cyano derivative. Similarly, dealkylation of III can be effected in known manner such as by treatment with cyanogen bromide followed by hydrolysis of the intermediate cyanamide or by treatment with a haloformate followed by hydrolysis of the urethane intermediate. In each instance the desired compound can be recovered employing conventional techniques.

The starting compounds, namely, the 5-cyano-5H-dibenzo[a,d]cycloheptene or its 10,11-dihydro derivative, either of which may be further substituted by X as defined above, may be prepared as described in a copending application of Marcia E. Christy, Case No. 9453, Ser. No. 422,510, filed Dec. 31, 1964.

The following examples are illustrative but not limitative of the invention.

EXAMPLE 1

5-Aminomethyl-5H-dibenzo[a,d]cycloheptene

A solution of anhydrous aluminum chloride (6.21 g., 0.0466 mole) in 75 ml. of anhydrous ether is added dropwise to a solution of lithium aluminum hydride (1.77 g., 0.0466 mole) in 50 ml. of absolute ether while stirring. An atmosphere of nitrogen is maintained in the apparatus and all vents are protected with drying tubes during the reaction. A solution of 5-cyano-5H-dibenzo[a,d]cycloheptene (10.13 g., 0.0466 mole) in 250 ml. of absolute ether is added dropwise with stirring (occasional warming of this solution may be necessary to prevent precipitation of the nitrile). The reaction mixture is stirred at 23–26° C. for 1 hour after the addition is complete. Water, 35 ml., then is added dropwise. Dilute sulfuric acid is added, causing precipitation of a white solid. The solid is collected, suspended in water and the mixture rendered strongly alkaline with sodium hydroxide solution. The filtrate also is rendered strongly alkaline and both mixtures, containing suspended solids are extracted separately with ether. Distillation of the ether from the combined extracts leaves a white solid residue, m.p. 95°–96.5° C., weighing 10.04 g. Recrystallization from hexane gives 8.71 g. of product, m.p. 97.5°–98.3° C. (sinters 97° C.). An analytical sample melts at 98–98.8° C. (sinters 97° C.).

Analysis, Calcd. for $C_{16}H_{15}N$: C, 86.84; H, 6.83; N, 6.33;

Found: C, 87.13; H, 6.87; N, 6.23

EXAMPLE 2

Following substantially the same procedure as Example 1 and replacing the 5-cyano-5H-dibenzo[a,d]cycloheptene of Example 1 with 5-cyano-dibenzocycloheptenes listed below there are obtained the products enumerated below.

| Starting Materials | Products |
| --- | --- |
| 5-Cyano-3-methyl-sulfonyl-5H-dibenzo[a,d]cycloheptene | 5-Aminomethyl-3-methyl-sulfonyl-5H-dibenzo[a,d]cycloheptene |
| 5-Cyano-3-dimethyl-sulfamoyl-5H-dibenzo[a,d]cycloheptene | 5-Aminomethyl-3-dimethyl-sulfamoyl[a,d]cycloheptene |
| 3-Chloro-5-cyano-10,11-dihydro-5H-dibenzo[a,d]cycloheptene | 5-Aminomethyl-3-chloro-10,11-dihydro-5H-dibenzo[a,d]cycloheptene |
| 5-Cyano-3-methyl-5H-dibenzo[a,d]cycloheptene | 5-Aminomethyl-3-methyl-5H-dibenzo[a,d]cycloheptene |

-continued

| Starting Materials | Products |
|---|---|
| 3-Chloro-5-cyano-5H-dibenzo[a,d]cycloheptene | 5-Aminomethyl-3-chloro-5H-dibenzo[a,d]cycloheptene |
| 5-Cyano-3-trifluoromethyl-5H-dibenzo[a,d]cycloheptene | 5-Aminomethyl-3-trifluoromethyl-5H-dibenzo[a,d]cycloheptene |
| 5-Cyano-3-methoxy-5H-dibenzo[a,d]cycloheptene | 5-Aminomethyl-3-methoxy-5H-dibenzo[a,d]cycloheptene |
| 5-Cyano-3-methylmercapto-5H-dibenzo[a,d]cycloheptene | 5-Aminomethyl-3-methylmercapto-5H-dibenzo[a,d]cycloheptene |

EXAMPLE 3

5-Formamidomethyl-5H-dibenzo[a,d]cycloheptene

5-Aminomethyl-5H-dibenzo[a,d]cycloheptene (4.82 g., 0.0218 mole) and methyl formate, 200 ml. are heated to 110° C. for 16½ hours in an autoclave. The yellow solution is evaporated to dryness on a film evaporator under reduced pressure. The residue is dissolved in benzene, the solution extracted with dilute hydrochloric acid, then with water and dried over anhydrous sodium sulfate. The benzene is evaporated and the residue dried to constant weight in a film evaporator under reduced pressure. The yellow solid residue weighs 5.49 g. and melts at 115°–117.5° C. to a cloudy melt, clearing at 119° C. Recrystallization from mixtures of benzene and hexane, followed by recrystallization from mixtures of ethanol and water gives a product melting at 120.3°–121° C. (clears 121.8° C.).

Analysis, Calcd. for $C_{17}H_{15}NO$: C, 81.90; H, 6.06; N, 5.62;

Found: C, 82.25, H, 5.85; N, 5.58.

EXAMPLE 4

Following substantially the same procedure of Example 3 and replacing the 5-aminomethyl-5H-dibenzo[a,d]cycloheptene of Example 3 with the 5-aminomethyl-dibenzocycloheptenes enumerated in Example 2 the following products are obtained:

5-Formamidomethyl-3-methylsulfonyl-5H-dibenzo[a,d]cycloheptene

3-Dimethylsulfamoyl-5-formamidomethyl-5H-dibenzo[a,d]cycloheptene

3-Chloro-10,11-dihydro-5-formamidomethyl-5H-dibenzo[a,d]cycloheptene

5-Formamidomethyl-3-methyl-5H-dibenzo[a,d]cycloheptene

3-Chloro-5-formamidomethyl-5H-dibenzo[a,d]cycloheptene

5-Formamidomethyl-3-trifluoromethyl-5H-dibenzo[a,d]cycloheptene

5-Formamidomethyl-3-methoxy-5H-dibenzo[a,d]cycloheptene

5-Formamidomethyl-3-methylmercapto-5H-dibenzo[a,d]cycloheptene

EXAMPLE 5

5-Methylaminomethyl-5H-dibenzo[a,d]cycloheptene hydrogen maleate

5-Formamidomethyl-5H-dibenzo[a,d]cycloheptene (3.80 g., 0.015 mole), dissolved in 400 ml. of absolute ether is added gradually to a solution of lithium aluminum hydride (0.87 g., 0.023 mole) in 45 ml. of absolute ether at a rate such that gentle refluxing is maintained. The reaction mixture, containing a precipitate, is heated to refluxing with stirring for 26 hours. After cooling to room temperature, 10 ml. of ethyl acetate is added to decompose the excess hydride. Water, 1 ml., 15% sodium hydroxide, 1 ml. and water, 3 ml. then are added to the vigorously stirred reaction mixture. After standing several days, the reaction mixture is filtered and the solid washed several times by suspension in ether. The combined filtrates and ether washings are evaporated on a film evaporator under reduced pressure, the pale yellow oily residue is dissolved in dilute hydrochloric acid, the solution extracted with ether to remove non-basic material, then rendered alkaline and the product extracted with ether. After washing with water and drying over anhydrous sodium sulfate, the ether is evaporated on a film evaporator under reduced pressure. The yellow oily residue weighs 3.05 g. A 2.95 g. portion is dissolved in isopropyl alcohol and a solution of 1.60 g. (0.0138 mole) of maleic acid in 5 ml. of isopropyl alcohol is added. The hydrogen maleate salt of the product separates out in white crystals. It melts at 163°–164° C. (clears, 165° C.) after further recrystallization from isopropyl alcohol and drying in vacuo over phosphorus pentoxide.

Analysis, Calcd. for $C_{17}H_{17}N \cdot C_4H_4O_4$: C, 71.78; H, 6.02; N, 3.99;

Found: C, 71.57; H, 6.02; N, 3.91.

EXAMPLE 6

Following substantially the same procedure of Example 5 and replacing the 5-formamidomethyl-5H-dibenzo[a,d]cycloheptene of Example 5 with the 5-formamidomethyl-dibenzocycloheptenes enumerated in Example 4 the following products are obtained:

5-Methylaminomethyl-3-methylsulfonyl-5H-dibenzo[a,d]cycloheptene

3-Dimethylsulfamoyl-5-methylaminomethyl-5H-dibenzo[a,d]cycloheptene

3-Chloro-10,11-dihydro-5-methylaminomethyl-5H-dibenzo[a,d]cycloheptene

3-Methyl-5-methylaminomethyl-5H-dibenzo[a,d]cycloheptene

3-Chloro-5-methylaminomethyl-5H-dibenzo[a,d]cycloheptene

5-Methylaminomethyl-3-trifluoromethyl-5H-dibenzo[a,d]cycloheptene

5-Methylaminomethyl-3-methoxy-5H-dibenzo[a,d]cycloheptene

5-Methylaminomethyl-3-methylmercapto-5H-dibenzo[a,d]cycloheptene

EXAMPLE 7

5-Dimethylaminomethyl-5H-dibenzo[a,d]cycloheptene hydrogen maleate

5-Aminomethyl-5H-dibenzo[a,d]cycloheptene (1.20 g., 0.0054 mole) is dissolved in 4.4 g. of 88% formic acid while cooling. Formaldehyde (1.5 ml. of a 37% solution) is added and the mixture heated in an oil bath at 95° C. Heating is interrupted when gas evolution becomes vigorous and resumed when it subsides. Heating is continued for 8 hours. After cooling to room temperature, 3 ml. of 4N hydrochloric acid is added and the mixture is evaporated to dryness on a film evaporator under reduced pressure. The residue is dissolved in water and the solution is rendered alkaline with sodium hydroxide solution. The product is extracted into benzene, the extract is washed with water and dried over anhydrous sodium sulfate. Evaporation of the benzene and drying the residue in a film evaporator under reduced pressure gives 1.34 g. of the yellow oily base. The base, 1.31 g. is dissolved in 10 ml. of isopropyl alcohol and a solution of 0.67 g. of maleic acid in 3 ml. of isopropyl alcohol is added. The hydrogen maleate separates and after the addition of ether, it is collected and recrystallized from isopropyl alcohol. The product melts at 169.8°–170.8° C. (clears 171.3° C.).

Analysis, Calcd. for $C_{18}H_{19}N \cdot C_4H_4O_4$: C, 72.31; H, 6.34; N, 3.83;
Found: C, 72.20; H, 6.42; N, 3.72;

EXAMPLE 8

Following substantially the same procedure of Example 7 and replacing the 5-aminomethyl-5H-dibenzo[a,d]cycloheptene of Example 7 with the 5-aminomethyl-dibenzocycloheptenes of Example 2 the following products are obtained:

5-Dimethylaminomethyl-3-methylsulfonyl-5H-dibenzo[a,d]cycloheptene

5-Dimethylaminomethyl-3-dimethylsulfamoyl-5H-dibenzo[a,d]cycloheptene

3-Chloro-10,11-dihydro-5-dimethylaminomethyl-5H-dibenzo[a,d]cycloheptene

5-Dimethylaminomethyl-3-methyl-5H-dibenzo[a,d]cycloheptene

3-Chloro-5-dimethylaminomethyl-5H-dibenzo[a,d]cycloheptene

5-Dimethylaminomethyl-3-trifluoromethyl-5H-dibenzo[a,d]cycloheptene

5-Dimethylaminomethyl-3-methoxy-5H-dibenzo[a,d]cycloheptene

5-Dimethylaminomethyl-3-methylmercapto-5H-dibenzo[a,d]cycloheptene

I claim:

1. The compound selected from the group consisting of a compound of the formula

wherein X is selected from the group consisting of hydrogen, halogen, lower alkyl, trifluoromethyl, lower alkoxy, lower alkylsulfonyl, lower alkylmercapto and dilower alkylsulfamoyl.

2. 5-Formamidomethyl-5H-dibenzo[a,d]cycloheptene.

3. 3-Dimethylsulfamoyl-5-formamidomethyl-5H-dibenzo[a,d]cycloheptene.

4. 5-Formamidomethyl-3-methylsulfonyl-5H-dibenzo[a,d]cycloheptene.

5. 5-Formamidomethyl-3-trifluoromethyl-5H-dibenzo[a,d]cycloheptene.

* * * * *